United States Patent [19]

Musser et al.

[11] Patent Number: 4,579,865
[45] Date of Patent: Apr. 1, 1986

[54] BENZOFURANYL CARBAMATES

[75] Inventors: John H. Musser, Malvern, Pa.; Charles A. Sutherland, Hawthorne, N.Y.

[73] Assignee: USV Pharmaceutical Corp., Tarrytown, N.Y.

[21] Appl. No.: 594,147

[22] Filed: Mar. 28, 1984

Related U.S. Application Data

[63] Continuation of Ser. No. 466,285, Feb. 14, 1983, abandoned.

[51] Int. Cl.$^4$ .................. C07D 307/79; A61K 31/34
[52] U.S. Cl. ...................................... 514/469; 514/470; 514/338; 514/375; 514/415; 549/466; 549/470; 549/51; 549/52; 549/55; 546/271; 548/217; 548/506
[58] Field of Search ............... 549/466, 467, 468, 470, 549/51, 52, 55; 424/275, 285

[56] References Cited

U.S. PATENT DOCUMENTS

| | | | |
|---|---|---|---|
| 3,471,170 | 10/1969 | Scharpf | 549/470 |
| 3,474,171 | 10/1969 | Scharpf | 549/470 |
| 3,547,955 | 12/1970 | Scharpf | 549/470 |
| 3,954,793 | 5/1976 | Hennessy | 548/371 |
| 4,032,649 | 6/1977 | Singerman | 549/51 |

Primary Examiner—Jane T. Fan

[57] ABSTRACT

Compounds of the structure;

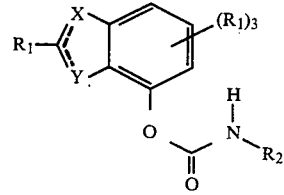

and pharmaceutically acceptable salts thereof, wherein:
  $R_1$ is H, alkyl, alkoxy, carboxyl, alkylcarboxy, trifluoromethyl, halogen, nitro or hydroxy;
  X is O, N, S or C;
  Y is O, N or S; and
  $R_2$ is H, alkyl, cycloalkyl, aryl or heteroaryl useful in the treatment of ischemic heart disease and hypertriglyceridemia.

9 Claims, No Drawings

BENZOFURANYL CARBAMATES

RELATED APPLICATION

This application is a continuation of our copending application Ser. No. 466,285, filed Feb. 14, 1983 now abandoned.

DESCRIPTION OF THE PRIOR ART

We have found that benzoheterocyclic carbamates are active antilipolytic agents as evidenced by the myocardial lipase and the rat adipocyte assays.

Lipolysis is associated with ischemic heart disease: free fatty acid has a detrimental effect on the ischemic heart by disrupting electrical conduction, decreasing myocardial efficiency and preventing the transfer of adosine diphosphate and adosine triphosphate, in and out, respectively, of the mitochondria. Interventions which depress myocardial oxygen consumption in animals and man provide a protective effect against ischemic injury.

The object of this invention is to provide compounds capable of inhibiting lipolysis associated with ischemic heart disease.

We have found that benzoheterocyclic carbamates are active antilipolytic agents, while the structurally related compounds N-(8-quinolinyl)carbamates are known in the prior art as fungicides, pesticides, amebicides and bactericides.

DESCRIPTION OF THE INVENTION

Compounds of the structure

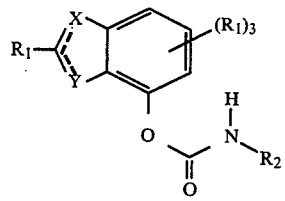

and pharmaceutically acceptable salts thereof, wherein:
  $R_1$ is H, alkyl, alkoxy, carboxyl, alkylcarboxy, trifluoromethyl, halogen, nitro or hydroxy;
  X is O, N, S or C;
  Y is O, N or S; and
  $R_2$ is H, alkyl, cycloalkyl having 5 to 6 carbon atoms, aryl, or heteroaryl, useful in the treatment of ischemic heart disease and hypertriglyceridemia.

The alkyl group and the alkyl moieties in alkoxy and alkylcarboxy contain from 1 to 10 carbon atoms and may be a straight or a branched chain. Such groups include methyl, ethyl, propyl, isopropyl, butyl isobutyl, amyl, isoamyl and the like.

The halogen is F, Cl, Br or I.

The aryl group such as phenyl and naphthyl and may be substituted with up to 3 members selected from the group consisting of H, alkyl, alkoxy, carboxyl, alkylcarboxy, trihalomethyl, halogen, nitro or hydroxy.

The heteroaryl is selected from the group consisting of tetrazoyl, pyridyl, furanyl, thienyl or imidazoyl.

The compounds of this invention may be readily prepared by art-recognized procedures from known starting materials and intermediates. The desired starting materials and intermediates can be prepared from readily available materials using standard organic reactions or alternatively, some starting materials and intermediates may be purchased from chemical supply companies, such as Aldrich and Pfaltz & Bauer.

Schematic procedures for the preparation of compounds of the present invention follow:

1.

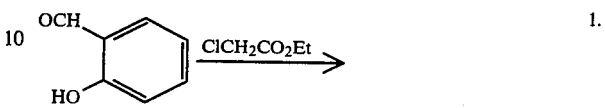

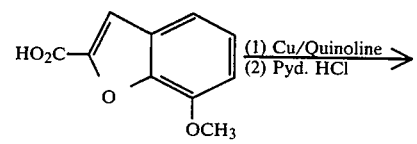

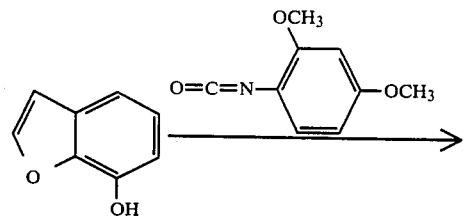

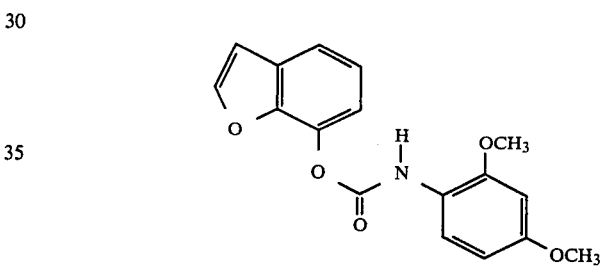

2.

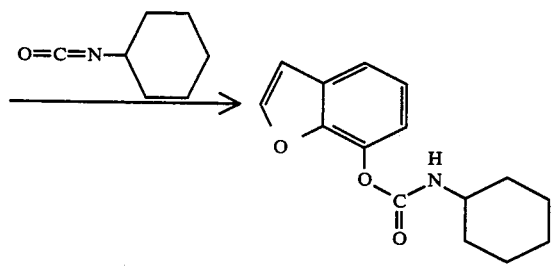

3.

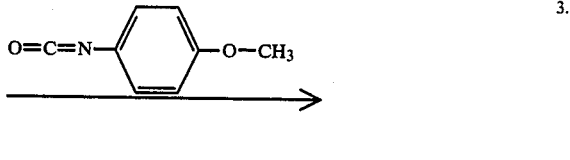

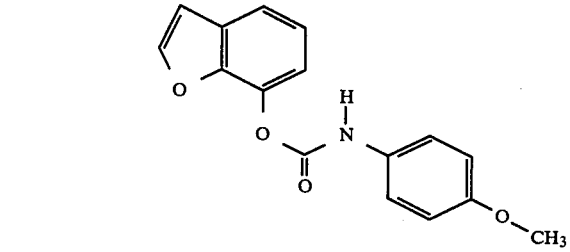

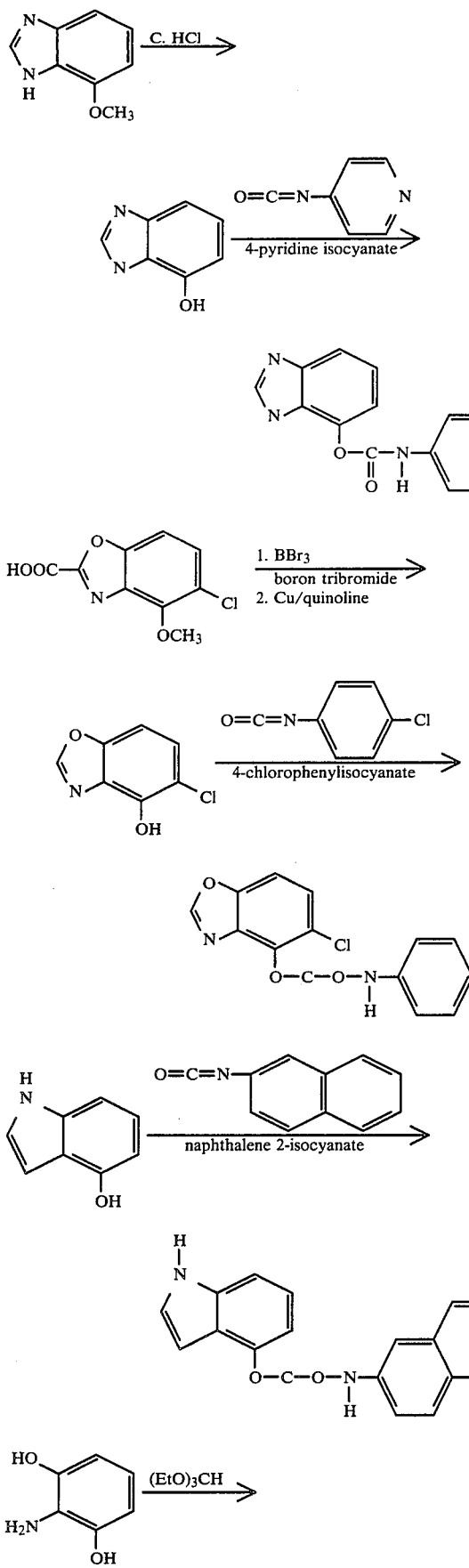

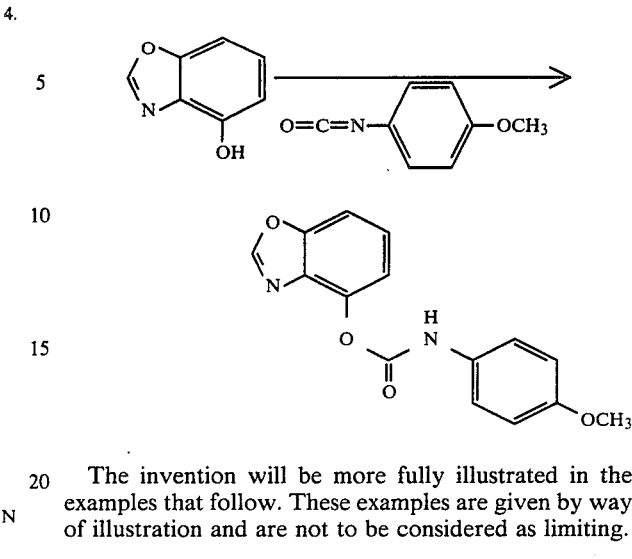

The invention will be more fully illustrated in the examples that follow. These examples are given by way of illustration and are not to be considered as limiting.

EXAMPLE 1A

7-Methoxybenzofuranyl-2-carboxylic acid

A mixture of 42 g. 2-vanillin (Aldrich 12080-4), 45 g. α-chloroethylacetate (Pfaltz & Bauer C12130), 75 g. potassium carbonate and 500 ml DMF was heated at 80° C. for 4 hours. The reaction was poured into ice and extracted with methylene chloride. The aqueous layer was acidified with hydrochloric acid and a precipitate formed. The precipitate was filtered and dried giving 27 g. (46% yield) of solid, m.p. >200° C.

EXAMPLE 1B

7-Methoxybenzofuran

To a solution of 7-methoxybenzofuranyl-2-carboxylic acid (2.6 g.) in quinoline (10 ml) was added finely ground copper metal. The reaction was slowly heated until the evolution of gas was noted. After termination of gas evolution, the mixture was cooled and diluted with methylene chloride. The solution was washed with 5% aqueous hydrochloric acid (six times); dried (MgSO$_4$) and concentrated to an oil, 1.8 g., (90% yield).

EXAMPLE 1C

7-Hydroxybenzofuran

A mixture of 7methoxybenzofuran (1.8 g.) and pyridine hydrochloride (4.6 g.) was heated at 220° C. for 2½ hours. The reaction was cooled and diluted with methylene chloride. The solution was washed with 5% aqueous hydrochloric acid (six times); dried (MgSO$_4$) and concentrated to an oil, 0.8 g. (50% yield).

EXAMPLE 1D

4-Hydroxybenzoxazole

A mixture of 2.1 g. 2-aminoresorcinol (Pfaltz & Bauer, A28620), 3.7 g. triethylformate and 0.1 g. sulfuric acid was heated at 130° C. for 30 minutes. After cooling, the remaining solid was recrystallized from ethyl acetate, 1.4 g. (62% yield).

EXAMPLE 1E

7-Benzofuranyl N-(4-methoxyphenyl)carbamate

To a solution of 7-hydroxybenzonfuran (0.7 g.) in ethyl ether (25 ml) and triethylamine (1 ml) was added 0.8 g. 4-methoxyphenyl isocyanate (Aldrich 23860-0). The reaction was stirred at room temperature for 3 days. The precipitate which forms was filtered and dried 0.8 g. (54% yield); m.p. 157°–159° C.

In like manner as above, using appropriate starting materials and reagents, the following compounds were prepared:

EXAMPLE 2

7-Benzofuranyl N-(2,4-dimethoxy)phenyl carbamate; m.p. 102°–103° C.

EXAMPLE 3

7-Benzofuranyl N-(cyclohexyl)carbamate; m.p. 149°–151° C.

EXAMPLE 4

4-Benzoxazoyl N-(4-methoxyphenyl)carbanamate; m.p. 161°–162° C.

Other benzoheterocyclic carbamates may be made as illustrated by the following examples:

EXAMPLE 5A

2-Nitro-3-benzyloxyphenylpyruvic Acid

A solution of 50 g. 3-hydroxy-2-nitrotoluene (Pfaltz & Bauer, NO9200), and 30 ml benzyl bromide in acetone is treated with excess potassium carbonate and refluxed for 2½ hours. The reaction is filtered and the solvent is removed in vacuo. The resulting ether is distilled. This compound (24 g.) is added to a solution of potassium ethoxide (4 g. potassium in ethanol) in ethyl ether (350 ml) and refluxed for 18 hours. The solvent is removed in vacuo and the remaining oil is treated with 1N NaOH at room temperature for 1 hour. The mixture is washed with ether (twice), acidified with hydrochloric acid yielding the desired product.

EXAMPLE 5B

7-Hydroxyindole

Reaction of 2-nitro-3-benzyloxyphenylpyruvic acid (2 g.) with 10% palladium on carbon (2 g.) in acetic acid under hydrogen atmosphere is complete in 30 minutes. The mixture is filtered and the solvent is removed in vacuo. The remaining material is dissolved in glycerol and heated at 220° C. for 20 minutes. The desired product is obtained by sublimation under high vacuum.

EXAMPLE 5C

7-Chloro-3-methylbenzo[b]thiophene

To a solution of 11.8 g. 2-chlorothiophenol (Aldrich, 15566-7) dissolved in aqueous sodium hydroxide (4.0 g./50 ml water) is added chloracetone (9.3 g.). After heating for 1 hour the reaction is cooled and extracted with methylene chloride. The extract is dried (MgSO$_4$) and concentrated to an oil. The oil is added to polyphosphoric acid (100 g.) and slowly heated to 120° C. The mixture is added to ice and extracted with ethyl ether. The ether extract is washed with water (twice); dried (MgSO$_4$) and concentrated to an oil. The oil is purified by distillation.

EXAMPLE 5D

7-Hydroxy-3-methylbenzo[b]thiophene

Cyclohexyl bromide (32.6 g.) and 7-chloro-3-methylbenzo[b]thiophene (18.3 g.) in THF (400 ml) is added to a suspension of magnesium turnings (7.3 g.) in THF. The mixture is stirred for two hours and heated on a steam bath for two hours. The reaction is cooled and oxygen is bubbled in slowly for two hours. The mixture is stirred for 18 hours at room temperature and extracted with chloroform. The organic extract is extracted with 5% sodium hydroxide. The aqueous extract is acidified with concentrated hydrochloric acid and extracted with ethyl ether. The ether extract is dried (MgSO$_4$) and concentrated to a solid.

EXAMPLE 5E

7-Hydroxybenzoxazole

A mixture of 2,3-dihydroxyaniline (2.5 g.), triethylorthoformate (4.5 g.) and 0.1 g. sulfuric acid is heated at 130° C. for one hour. After cooling, the remaining material is purified by HPLC on silica gel.

In like manner as above, using the appropriate starting materials and reagents, the following compounds can be prepared:

EXAMPLE 5F 4-hydroxybenzthiazole

EXAMPLE 5G

7-Hydroxybenzthiazole

EXAMPLE 5H 1-methyl-4-hydroxybenzimidazole

EXAMPLE 5I

7-Indolyl N-(4-methoxyphenyl)carbamate

To a solution of 7-hydroxyindole (0.7 g.) in ethyl ether (25 ml) and triethylamine (1 ml) is added 0.8 g. 4-methoxyphenyl isocyanate (Aldrich 23860-0). The reaction is stirred for 3 days at room temperature. The solvent is removed in vacuo and the remaining oil is purified by HPLC on silica gel.

In like manner as above, using appropriate starting materials and reagents, the following compounds can be prepared:

EXAMPLE 6

7-Indolyl N-(4-methoxyphenyl)carbamate.

EXAMPLE 7

7-Indolyl N-(3-trifluoromethylphenyl)carbamate.

EXAMPLE 8

7-Indolyl N-(3-nitrophenyl)carbamate.

EXAMPLE 9

7-Indolyl N-(2-chlorophenyl)carbamate.

EXAMPLE 10

7-Indolyl N-(2-bromophenyl)carbamate.

EXAMPLE 11

3-Methyl-7-benzo[b]thiophenyl N-(4-methoxyphenyl)carbamate.

EXAMPLE 12

3-Methyl-7-benzo[b]thiophenyl N-phenylcarbamate.

EXAMPLE 13

3-Methyl-7-benzo[b]thiophenyl N-(4-dimethylaminophenyl)carbamate.

EXAMPLE 14

3-Methyl-7-benzo[b]thiophenyl N-(3-acetylphenyl)carbamate.

EXAMPLE 15

7-Benzoxazolyl N-(4-methoxyphenyl)carbamate.

EXAMPLE 16

7-Benzoxazolyl N-cyclopentylcarbamate.

EXAMPLE 17

4-Benzothiazolyl N-(4-methoxyphenyl)carbamate.

EXAMPLE 18

4-Benzothiazolyl N-(2-cyanophenyl)carbamate.

EXAMPLE 19

7-Benzothiazolyl N-(4-methoxyphenyl)carbamate.

EXAMPLE 20

7-Benzothiazolyl N-(4-acetamidophenyl)carbamate.

EXAMPLE 21

1-Methyl-7-Benzimidazolyl N-(4-methoxyphenyl)carbamate.

EXAMPLE 22

1-Methyl-7-Benzimidazolyl N-(3-carbomethoxyphenyl)carbamate.

The compounds of the present invention exhibited activity in the myocardial lipase assay, the rat adipocyte assay and the in vivo lipolysis assay.

Myocardial Lipase Assay

All compounds were dissolved in DMSO (final concentration 3.0%) and tested in duplicate at a concentration of 100 μM. Canine cardiac lipases were obtained by extracting washed heart membranes with buffer plus heparin and a small amount of Triton X-100 detergent. Because these enzymes are only active at an oil-water interface, the enzyme reaction is run in an oil-water emulsion that contains triolein substrate, Tris buffer (50 mM, pH 6.8) and a small amount of bovine serum albumin (0.5%) added to stabilize the emulsion. A small amount of tritiated triolein was added to the unlabelled triolein substrate. Tritium-labelled oleic acid released by the lipases was extracted into hexane, separated from unreacted triolein and counted in a scintillation counter. Inhibitory agents reduce the amount of radioactivity appearing in the free fatty acid fraction isolated in the extraction procedure.

Rat Adipocyte Assay

Abdominal fat pads were removed from male rats weighing 200-250 grams and placed in Krebs-bicarbonate buffer gassed with 95% $O_2$/5% $CO_2$. The fat pads were digested with collagenase for 1 hour at 37° C., washed twice with Krebs-bicarbonate buffer and distributed among a set of 20 ml plastic counting vials. Two such vials received only buffer and cells (4 ml) but no agonists or antagonists. The remaining vials received epinephrine (3 μM) plus the phosphodiesterase inhibitor methylisobutylxanthine (10 μM). Test compounds were dissolved in DMSO or water to a concentration of 20 μM and 40 μl was added to the buffer plus cells in the counting vials. The final compound concentration for routine screening was 200 μM (final concentration of DMSO=1%).

The cells were incubated for 1 hour at 37° C. under a 95% $O_2$/5% $CO_2$ atmosphere. The incubation was stopped by placing the vials in crushed ice. The cells and medium were transferred to test tubes, centrifuged and the cell layer removed by aspiration. The aqueous phase was assayed for glycerol using the enzyme glycerol dehydrogenase. The glycerol dihydrogenase assay for glycerol depends on the enzyme catalyzed conversion of glycerol to glyceraldehyde and NAD to NADH. The assay can detect as little as 5-10 nanomoles of glycerol. The aqueous phase, following removal of cells, usually contained about 50 to 80 nanomoles of glycerol per 300 μl of assayed sample if no inhibitory activity was present. Samples from the control tubes (no agonist) usually contained 0-5 nanomoles of glycerol per 300 μl of sample.

In Vivo Lipolysis Assay

This assay is based on the general concepts described by Lovisolo et al. Lovisolo, P. P., Briatico-Vangosa, G., Orsini, G., Ronchi, R. and Angelucci, R. Pharmacological profile of a new antilipolytic agent: 5-methylpyrazine-2-carboxylic acid-4-oxide (Acipimox) II—antilipolytic and blood lipid lowering activity. Pharmacological Research Communications 13;163-174(1981).

Sixteen male rats (200-300 grams) are marked with a color code to facilitate individual identification during the course of the experiment. Each assay is to include 4 nonfasted control animals.

The remaining animals are fasted for 22 hours (water ad libitum). Test compounds are prepared either in methocel (S-2) or methocel plus DMSO (S-3). After 22 hours of fasting the animals are injected i.p. at five minute intervals with either 2 ml of carrier solution (S-2 or 3) or 2 ml of carrier solution plus test compound. This procedure is carried out on animals lightly anesthetized with ether.

Two hours after drug injection, at 5 min intervals, the animals are again lightly anesthetized and the abdominal cavity is opened. Blood is withdrawn from the inferior vena cava through a 16 gauge needle into a 20 ml syringe. No anticoagulant is used. The blood is transferred immediately to 12 ml plastic centrifuge tubes. The blood is allowed to coagulate at room temperature for 1 hour. These tubes are then centrifuged at 4000×g (3000 rpm) for 10 min in an RC-3 Sorval refrigerated centrifuge. The clear serum (3-4 ml/sample) is transferred to the siliconized vacutainer tubes, labeled and stored at −70° C. The serum samples are analyzed for determination of unesterified fatty acids.

The results obtained on representative compounds of the present invention are shown in Table I.

TABLE I

INHIBITION OF MYOCARDIAL LIPASE, RAT ADIPOCYTE LIPOLYSIS AND IN VIVO LIPOLYSIS BY BENZOHETEROCYCLIC CARBAMATES

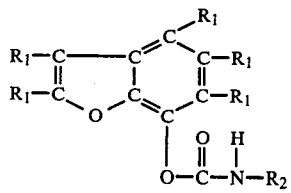

| # | X | Y | R₂ | Lipase $I_{50}$ μM | Adipocyte $I_{50}$ μM | In Vivo Lipolysis % Inhib. at mg/Kg |
|---|---|---|---|---|---|---|
| 1 | CH | O | 4-methoxyphenyl | 16 | 0.3 | 97 @ 25 p.o. |
| 2 | CH | O | 2,4-dimethoxyphenyl | 40 | 0.3 | 71 @ 100 p.o. |
| 3 | CH | O | cyclohexyl | 10 | 12.0 | 26 @ 100 p.o. |
| 4 | O | N | 4-methoxyphenyl | 79 | 2.4 | 40 @ 100 i.p. |

The therapeutic compounds of this invention may be administered to a mammal alone or in combination with pharmaceutically acceptable carriers, the proporation of which is determined by the solubility and chemical nature of the compound, chosen route of administration and standard pharmaceutical practice.

The physician will determine the dosage of the present therapeutic agents which will be most suitable and it will vary with the form of administration and the particular compound chosen, and also, it will vary with the particular patient under treatment. He will generally wish to initiate treatment with small dosages substantially less than the optimum dose of the compound and increase the dosage by small increments until the optimum effect under the circumstances is reached. The therapeutic dosage will generally be from a couple of mg to about 30 mg/kg of body weight or higher.

What is claimed is:

1. A compound of the formula

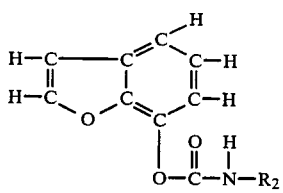

or a pharmaceutically acceptable salt thereof wherein
each $R_1$ is hydrogen, alkyl, alkoxy, halogen and hydroxy, wherein at least one $R_1$ is hydrogen;
$R_2$ is hydrogen, alkyl, cycloalkyl having 5 to 6 carbon atoms, phenyl or naphthyl;
wherein
said alkyl and the alkyl moiety in alkoxy contain from 1 to 10 carbon atoms.

2. A compound of the formula wherein
$R_2$ is cyclopentyl, cyclohexyl, methoxyphenyl, or dimethoxyphenyl.

3. The compound of claim 2 which is 7-benzofuranyl N-(4-methoxyphenyl)carbamate.

4. The compound of claim 2 which is 7-benzofuranyl N-(2,4-dimethoxyphenyl)carbamate.

5. The compound of claim 2 which is 7-benzofuranyl N-cyclohexylcarbamate.

6. A pharmaceutical composition for the treatment of ischemic heart disease in a mammal comprising an effective amount of the compound of claim 1 and a pharmaceutically acceptable carrier.

7. A pharmaceutical composition for the treatment of ischemic heart disease in a mammal comprising an effective amount of the compound of claim 2 and a pharmaceutically acceptable carrier.

8. A method of treating ischemic heart disease in a mammal by administering to said mammal an effective amount of the composition of claim 6.

9. A method of treating ischemic heart disease in a mammal by administering to said mammal an effective amount of the composition of claim 7.

* * * * *